(12) United States Patent
Schuette et al.

(10) Patent No.: US 8,376,965 B2
(45) Date of Patent: Feb. 19, 2013

(54) METHOD AND APPARATUS FOR USING BIOPOTENTIALS FOR SIMULTANEOUS MULTIPLE CONTROL FUNCTIONS IN COMPUTER SYSTEMS

(75) Inventors: Franz Michael Schuette, Colorado Springs, CO (US); Andrew Junker, Yellow Springs, OH (US)

(73) Assignees: BCInet, San Jose, CA (US); Brain Actuated Technologies, Yellow Springs, OH (US)

( * ) Notice: Subject to any disclaimer, the term of this patent is extended or adjusted under 35 U.S.C. 154(b) by 36 days.

(21) Appl. No.: 12/957,585

(22) Filed: Dec. 1, 2010

(65) Prior Publication Data

US 2011/0301488 A1 Dec. 8, 2011

Related U.S. Application Data

(62) Division of application No. 12/406,405, filed on Mar. 18, 2009, now abandoned.

(60) Provisional application No. 61/037,723, filed on Mar. 19, 2008.

(51) Int. Cl.
*A61B 5/103* (2006.01)
*A61B 5/117* (2006.01)
*A61B 5/04* (2006.01)
*A61B 5/05* (2006.01)

(52) U.S. Cl. ......... 600/587; 600/595; 600/546; 600/547

(58) Field of Classification Search .......... 600/544–547, 600/558, 587, 595; 702/127, 138–154
See application file for complete search history.

(56) References Cited

U.S. PATENT DOCUMENTS

| | | | | |
|---|---|---|---|---|
| 5,692,517 A * | 12/1997 | Junker | ................... | 600/545 |
| 6,014,582 A * | 1/2000 | He | ................... | 600/544 |
| 6,032,072 A * | 2/2000 | Greenwald et al. | .......... | 600/544 |
| 6,085,115 A * | 7/2000 | Weaver et al. | ................ | 600/509 |
| 6,636,763 B1 * | 10/2003 | Junker et al. | ................ | 600/545 |
| 6,728,564 B2 * | 4/2004 | Lahteenmaki | ............... | 600/383 |
| 6,795,724 B2 * | 9/2004 | Hogan | ................... | 600/545 |
| 6,950,698 B2 * | 9/2005 | Sarkela et al. | ............... | 600/544 |
| 7,035,686 B2 * | 4/2006 | Hogan | ................... | 600/545 |
| 7,206,625 B2 * | 4/2007 | Kurtz et al. | ................... | 600/372 |
| 2006/0155576 A1 * | 7/2006 | Deluz | ................... | 705/2 |

* cited by examiner

*Primary Examiner* — Jeffrey G Hoekstra
(74) *Attorney, Agent, or Firm* — Hartman GlobalIP Law; Gary M. Hartman; Domenica N. S. Hartman (57) ABSTRACT

A biosignal-computer-interface apparatus and method. The apparatus includes one or more devices for generating biosignals based on at least one physiological parameter of an individual, and a computer-interface device capable of performing multiple tasks, including converting the biosignals into at least one input signal, establishing a scale encompassing different levels of the input signal, multiplying the input signal into parallel control channels, dividing the scale into multiple zones for each of the parallel control channels, assigning computer commands to each individual zone of the multiple zones, and generating the computer command assigned to at least one of the individual zones if the level of the input signal is within the at least one individual zone. The individual zones can be the same or different among the parallel control channels.

12 Claims, 6 Drawing Sheets

METHOD AND APPARATUS FOR USING BIOPOTENTIALS FOR SIMULTANEOUS MULTIPLE CONTROL FUNCTIONS IN COMPUTER SYSTEMS

CROSS REFERENCE TO RELATED APPLICATIONS

This is a division patent application of co-pending U.S. patent application Ser. No. 12/406,405, filed Mar. 18, 2009.

BACKGROUND OF THE INVENTION

The present invention generally relates to computer-related technology, and more particularly to the use of biosignals of a user wishing to control a computer-controllable activity or operation, including computer games.

Brain-computer interface (BCI) or Neural Interface (NI) devices that fall into the general category of Biosignal Interface (BI) technology are gaining increasing importance for controlling electronic systems, a notable example of which is computers. Applications include biomedical appliances such as wheelchair and sailboat controls, as well as communication devices allowing, for example, conversion of eye positions to keystrokes of a word processing device. Other applications include biofeedback devices aimed at the control of emotional states, and NI devices to control computer games. In the broadest sense, even voice recognition can be considered as a biosignal interface.

Biopotentials generally result from the activity-dependent change of ionic composition of any cell's cytoplasm. In an idle state, all living cells are at a resting potential, typically −20 to −80 mV across their membranes versus the extracellular space. Excitation of any cell results in opening of selective ion channels, starting with fast sodium channels and calcium channels, allowing extracellular Na+ to enter the cell's cytoplasm and thereby depolarize the cell to a typical range of about +100 to about +150 mV compared to the extracellular fluid. If this type of excitation happens in multiple cells simultaneously, extracellular electrodes can sense the difference in charge and the resulting electrode output signals can be recorded. This type of biopotential and changes thereof are the basis for a variety of diagnostic tools, such as electrokardiogram (EKG), electromyogram (EMG) and electroencephalogram (EMG). The exploitation of biopotentials beyond the diagnostic applications is emerging in prosthetic limbs, where nerve signals can be measured and converted into control signals for governing mechanical movement of artificial limbs. In addition, biofeedback has been used for the purpose of facilitating meditation or preparing athletes for sporting events. A relatively new use of biosignals includes their use in computer games as a novel contribution to virtual reality sensation.

In the general field of using brain-based measurements as the source of biopotentials for diagnostic purposes, three different principles have emerged based on the type of sensor used, namely, sensors or sensor arrays adapted for implantation into the brain (invasive sensors), implantation into the skull and against the gray matter of the brain (partially invasive), or non-invasive placement meaning that the electrodes are simply placed on the skin. Invasive sensors have been used to alleviate the lack of functionality in individuals that suffer from some type of disability, for example, as described by Hochberg et al., "Neuronal ensemble control of prosthetic devices by a human with tetraplegia," Nature 442: 164-171 (13 Jul. 2006). Most invasive sensors are derivatives of the "Utah Array" developed by Richard A. Norman at the University of Utah, using approximately one hundred hair-thin electrodes to record extracellular potentials. In commercial applications, the Cyberkinetics "Braingate" is a device that uses invasively implanted electrodes to control wheelchairs and other devices. Likewise, partially invasive systems have already proven functional to play video games. In contrast, non-invasive electrodes have typically been limited to use for therapeutic purposes. As taught in U.S. Pat. Nos. 6,795,724 and 7,035,686, biofeedback using color-based neurofeedback has been employed based on the assignment of different colors on a computer screen to different states of neuronal activity.

Non-invasive electrodes generally need greater spatial separation for de-convoluting spatial properties of recorded signals as described in U.S. Pat. No. 6,014,582 or using near-field and far-field signals as described in U.S. Pat. No. 6,032,072. U.S. Pat. No. 6,950,698 discloses a five or seven electrode array and the positioning of the array on the forehead of a patient to optimally separate EOG, EEG and EMG signals. U.S. Pat. No. 7,206,625 to Kutz et al. discloses a compact measuring apparatus wherein the amplifier is directly adjacent to the sensors to reduce antenna effects and improve the signal to noise ratio. U.S. Pat. No. 6,728,564 discloses a system configurable to use a classical one-channel approach or else to alternately switch between predefined parts of the sensor array to simulate a two-channel system for EEG and EMG measurements. The Emotiv EPOC system employs a sensor array integrated into a helmet-like structure to convert the amplitudes of EEG signals into levitation of given objects in computer games and rotating the objects using rotational signals created by a gyroscope built into the headset.

A recurring issue associated with the use of biosignals is that it can be relatively difficult for a given user to control his or her brain activity. Alpha, beta and gamma brain waves are readily accessible for sensing with EEG sensors or related devices and can be separated into subgroups based on frequency properties. However, for most individuals it is very difficult to arbitrarily influence activity of selected subgroups of brain waves, especially in a time-controlled fashion. Timing of signals however is critical for most control functions, regardless of whether they are used for navigation systems or within another computer-related application. A case in point is the use of biosignals in gaming applications to trigger, for example, shooting or jumping in first person shooter (FPS) games.

In contrast to true brain waves, muscle signals can be readily and arbitrarily triggered, regardless of whether they relate to facial movements or, for example, eye movements. On the other hand, electrical muscle signals are difficult to separate into different channels, and tend to propagate across the body making it difficult to distinguish their precise origin. Even if accomplished, the user is posed with a somewhat difficult task of acquiring the necessary skills to master the exercise of different muscles without crossing over between groups.

BRIEF DESCRIPTION OF THE INVENTION

The present invention describes an apparatus and method for using biosignals of an individual to control a computer-related technology, by which multiple instances of a single or a group of substantially identical signals are able to be converted into multiple, complex command functions using signal duplication into multiple parallel channels operable as individual computer input/control devices.

According to a first aspect of the invention, a biosignal-computer-interface apparatus is provided that includes means for generating biosignals based on at least one physiological parameter of an individual, and computer-interface means for performing multiple tasks, including converting the biosignals into at least one input signal, establishing a scale encompassing different levels of the input signal, multiplying the input signal into parallel control channels, dividing the scale into multiple zones for each of the parallel control channels, assigning computer commands to individual zones of the multiple zones, and generating the computer command assigned to one or more of the individual zones if the level of the input signal is within that individual zone. The individual zones can be the same or different among the parallel control channels in terms of the number of individual zones and ranges of the scale covered by the individual zones.

According to a second aspect of the invention, the method includes converting biosignals into at least one input signal, assigning multiple computer commands to multiple individual zones of multiple parallel control channels, generating at least one of the computer commands if the input signal exceeds a threshold of at least one of the individual zones of the parallel control channels, and simultaneously generating the computer commands assigned to two or more of the individual zones of two or more of the parallel control channels if the input signal is within the two or more individual zones.

The computer-interface means may be any of a variety of equipment well known in the computer-related art, including a general-purpose or special-purpose computer on which specialized software is running to perform the multiple tasks, or peripheral computer hardware, specialized hardware, or any other computing/processing equipment that can be manufactured or modified to be programmed and configured for performing the multiple tasks through or with a computer or any other computer-related technology. Though it is foreseeable that invasive and partially-invasive electrodes could be employed by the invention, a particular aspect of the invention is the ability to use biosignals generated by non-invasive types of electrodes adapted for monitoring a variety of physiological parameters, including biopotentials associated with muscle activity, to generate output signals capable of controlling electronic systems, nonlimiting examples of which include gaming and other applications running on computers, communication devices, vehicles, weapon systems, etc. The invention achieves more differentiated controls over a given electronic system based on assigning multiple different commands to multiple individual zones of multiple parallel control channels whose individual zones may overlap. In this manner, it is possible to use a single biosignal as an input to produce simple individual commands as well as complex commands corresponding to combinations of individual commands. In particular, if the biosignal is at a level coinciding with two overlapping zones of two parallel control channels, the apparatus and method are capable of generating a complex control signal from the single biosignal as a result of the biosignal being the basis for the input to both parallel control channels and then generating a command that is a combination of the individual commands assigned to the overlapping zones.

Other aspects and advantages of this invention will be better appreciated from the following detailed description.

DETAILED DESCRIPTION OF THE INVENTION

The present invention provides a method and apparatus that can be used to convert multiple instances of a single biosignal or a group of substantially the same biosignals into multiple, complex command functions using signal duplication into multiple parallel channels that effectively serve as separate computer controller devices, each divided into several operational zones. The zones of one control channel can overlap with zones in other control channels. In this manner, simultaneous commands can be created by binding, for example, different keyboard characters to overlapping zones of two or more control channels. A variety of sources are contemplated for the biosignals, though of particular interest are biopotentials, that is, electrical discharges resulting from excitation or relaxation of nerve, muscle or skin cells.

An example of implementing the present invention will be described in reference to the dynamic range of electrical potentials that can be obtained by sensing tension in one or more groups of the user's muscles, for example, the facial muscles of a human, using a single electrode or more preferably an array of electrodes. The dynamic range of electrical potentials can be assigned to a tension scale of, for example, 0 to 100 where 0 corresponds to substantially complete muscle relaxation and 100 corresponds to a high excitation of the muscles. This scale of 1 to 100 can be referred to as a biosignal input joystick, though it should be understood that the muscle-based biosignal can be broadly utilized as, in effect, a variety of different types of computer input/controller devices. In a simple example, the scale of the biosignal input joystick can be divided into different input zones, and each input zone can be bound to a particular control function so that if the level of muscle tension is within a given zone, a particular command signal is generated that is associated with that control function. For example, the control function can be a keystroke that specifies a specific action in a computer game, common examples of which include pressing the "W"

key to move forward (for example, the user's computer graphic representation (avatar) of himself or herself), pressing the "S" key to move backward, pressing the spacebar to jump, and similar typical key bindings used to control computer games through a computer keyboard. Whenever the signal transcends from one input zone to another, the control signal changes to another key binding corresponding to another specific action, which may be a different keystroke or the same keystroke with a different mode of use, for example, a single actuation (press and release), a dwell, a hold time duration, a repeat interval, etc., as evidenced by the nonlimiting variety of modalities included in the pull-down list in FIG. 2. After leaving an input zone, the corresponding control signal is terminated by the subsequent control signal associated with the new input zone, resulting in a single control signal being transmitted.

In computer gaming applications, many actions require combinations of different key strokes to achieve desired actions. For example, in order to jump forward, it is necessary to press the jump (spacebar) key and the forward ("W") key simultaneously. Likewise, jumping backwards requires simultaneous pressing of the "spacebar" and "S" key. These actions can be achieved with the present invention by multiplying a single biosignal input joystick (for example, tension in a single group of muscles) into several control channels, each with multiple input zones. The input zones of the control channels can be defined and actuated in parallel, and different keystrokes and modalities (e.g., single, dwell, hold, repeat, etc.) can be assigned to the input zones independently of each other and with different level thresholds.

In the following description, the invention will be described in the context of its implementation in computer games and gaming applications. For the convenience of the discussion, the following keystrokes will be assumed to be bound to the following specific actions: the "W" key for moving forward, the "S" key for moving backward, the "A" key for moving to the left, the "D" key for moving to the right, and the spacebar for jumping. While the present invention is well suited for gaming using keyboard inputs, it is foreseeable that the invention can be implemented in a variety of other computer-related and computer-controlled activities and operations that may be used for entertainment, diagnostic, or control-related purposes. Notable examples are the control of communication devices (e.g., word processors), vehicles (e.g., wheelchairs), and weapon systems.

Figure 1:
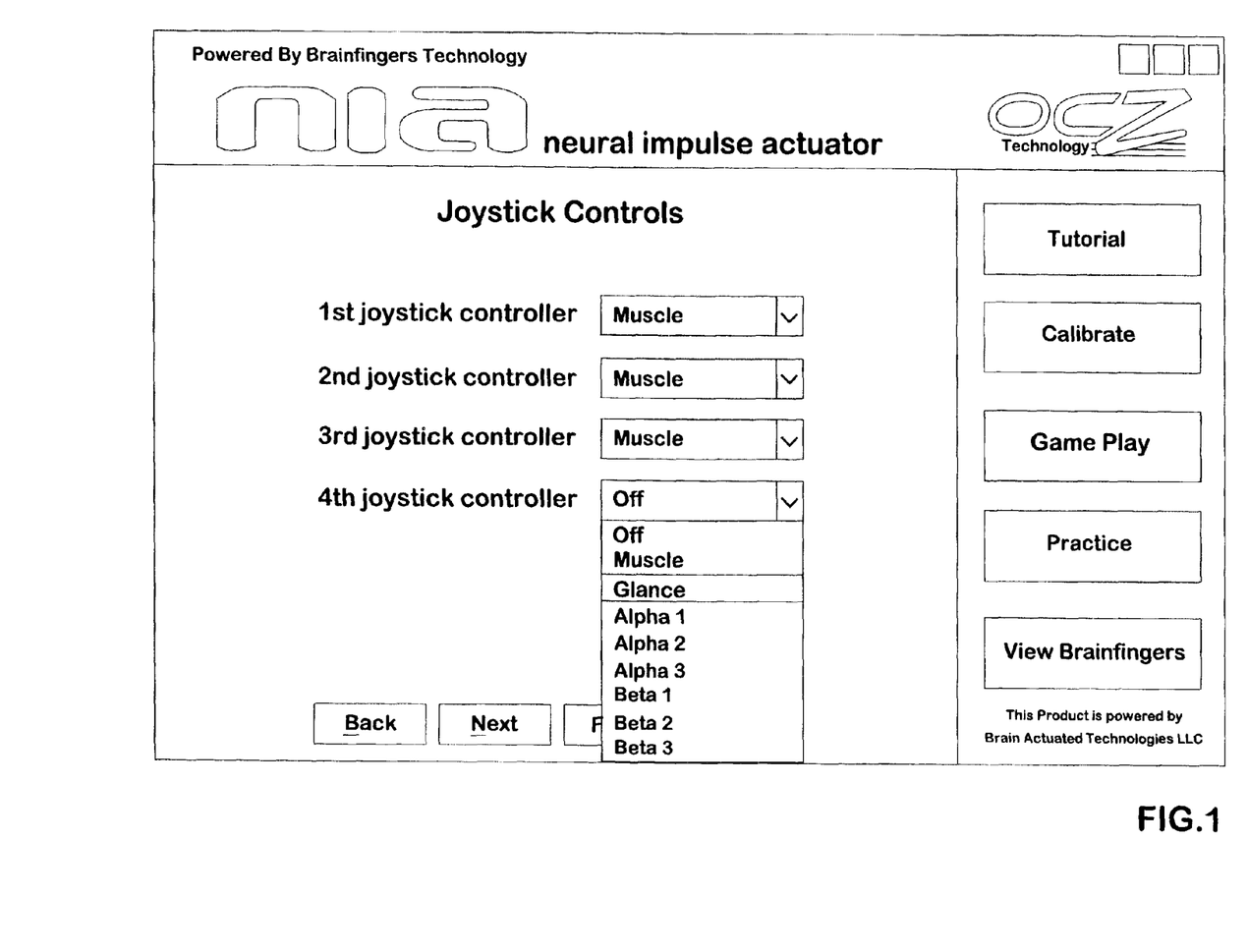
FIG. 1 is a screen shot of a configuration panel generated by software adapted for controlling a gaming application through multiple parallel control channels on the basis of a single biological-generated signal, wherein the source of the signal has been selected as the biopotential of a muscle or group of muscles.
Figure 2:
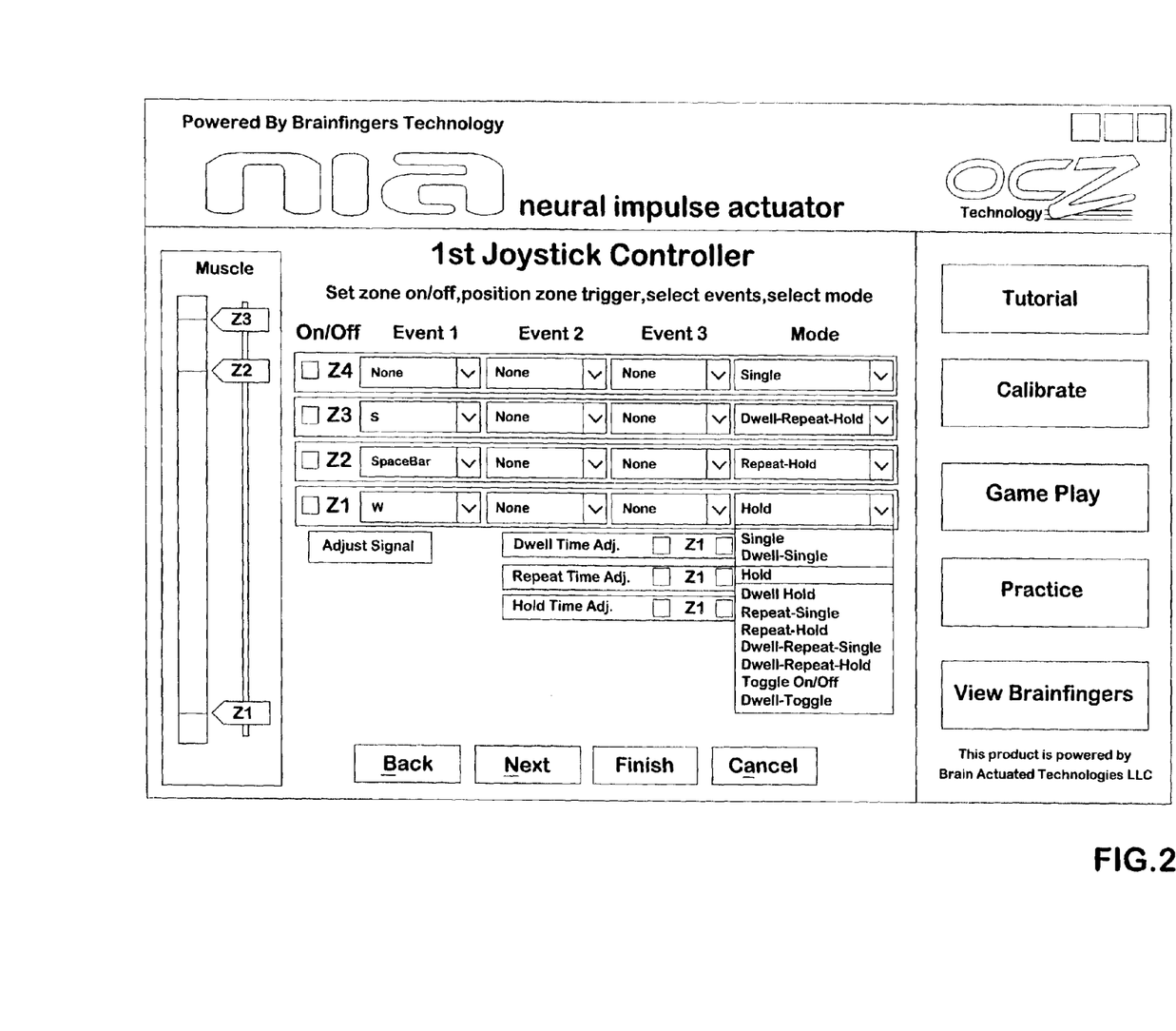
FIG. 2 is another screen shot of a configuration panel generated by the software, and shows the manner in which a first of the parallel control channels of FIG. 1 is configured into four individual zones: no action for inputs below the threshold of a first zone (Z1) assigned to the keyboard character "W", and actuation of the keyboard characters "W," "SpaceBar" and "S" for inputs within first, second and third zones (Z1, Z2, and Z3), respectively.
Figure 3:
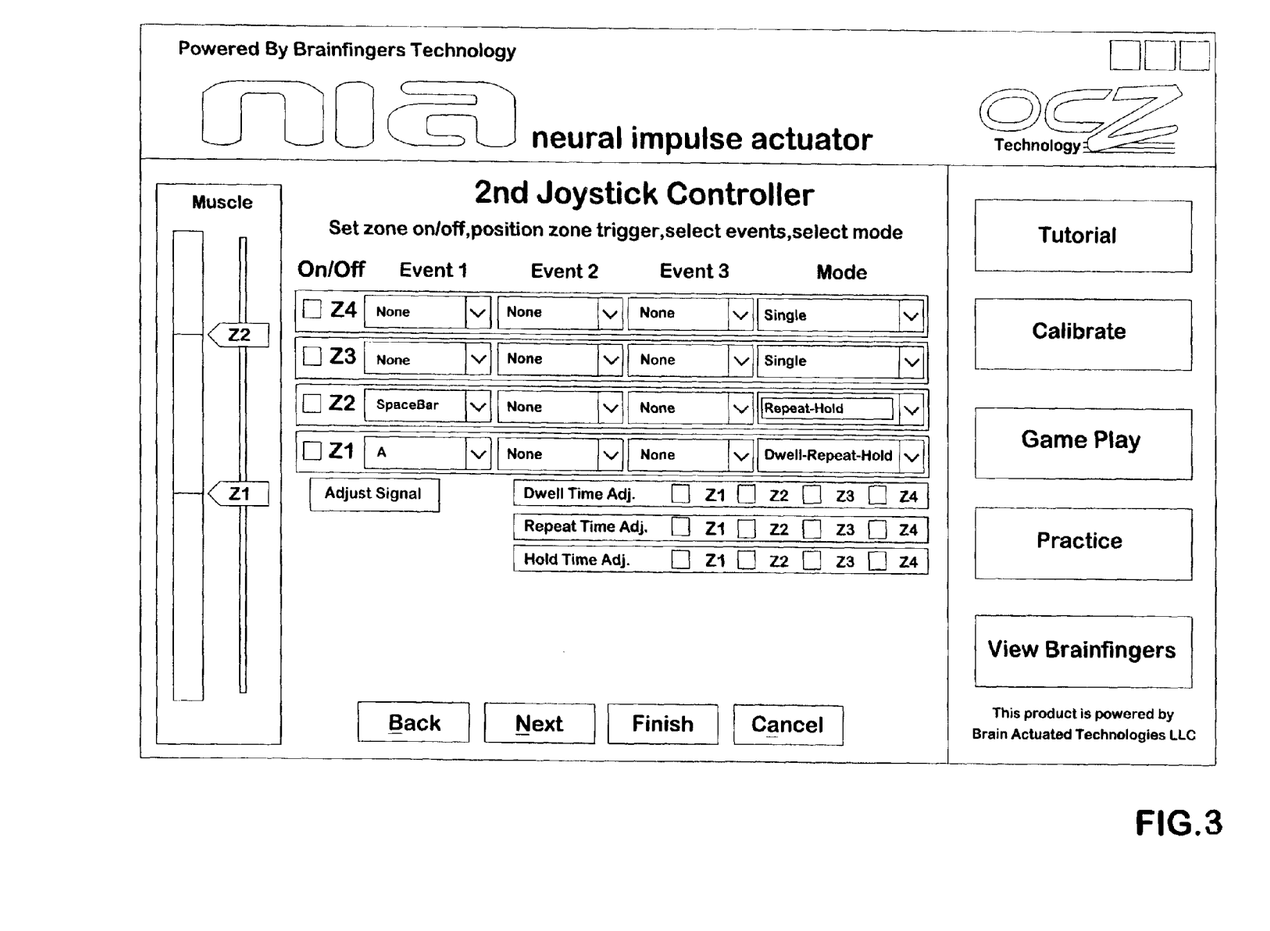
FIGS. 3 and 4 are additional screen shots of configuration panels generated by the software, which show the assignment of keyboard characters for the second and third control channels of FIG. 1, respectively, wherein "A" and "D" of the second and third control channels, respectively, are assigned to the same zone (Z1) and "spacebar" of both channels is assigned to another zone (Z2).

As an illustrative example, FIG. 1 shows a configuration panel generated by software adapted for controlling a gaming application capable of using up to four control channels, identified as "joystick controllers," on the basis of a single biosignal (while the term "joystick" will be used, it should be understood that the controllers could be used to simulate other computer input/controller devices). The panel shows the biosignal in the process of being selected as a muscle source from a list of possible sources that include alpha and beta brain waves, by which brain activity could be monitored as an input. In FIG. 2, a first of the joystick controllers is in the process of being configured so that the "W" keystroke (input) for the game will be activated with a "Hold" modality when the level of the signal is within a first zone (Z1) of the tension scale that has been associated with the biosignal obtained from the chosen muscle group. Furthermore, the "spacebar" key input for the game will be activated with a "Repeat-Hold" modality if the level of the signal exceeds the upper limit of Z1, coinciding with a lower threshold for the next higher second zone (Z2) of the tension scale associated with the same muscle group, and the "S" key input for the game will be activated with a "Dwell-Repeat-Hold" modality when the level of the signal exceeds the lower threshold for the next higher third zone (Z3) corresponding to the highest level of the tension scale. FIGS. 2 and 3 show additional configuration panels by which additional keystrokes and/or modalities are bound to tension zones that lie within or overlap the zones assigned to the first controller. For example, the second controller has been configured so that its first zone (Z1) lies entirely within the first zone (Z1) of the first controller, but for a different keystroke and modality: the "A" keyboard character and a "Dwell-Repeat-Hold" modality. Furthermore, the second zone (Z2) of the second controller has been configured so that the excitation level associated with Z2 overlaps the first, second and third zones (Z1, Z2 and Z3) of the first controller. The keystroke associated with Z2 of the second controller is the same as Z2 of the first controller (the "spacebar" signal) and the same modality ("Repeat-Hold"), but is different than the keystrokes associated with Z1 (the "W" key) and Z3 (the "S" key) of the first controller.

Based on the programming of the first and second controllers described above and shown in FIGS. 2 and 3, if the muscle tension level within the muscle group is within Z1 of the first controller but below Z1 of the second controller, only the W key is actuated in accordance with the programming for the first controller. In the present example, this keystroke is associated with a forward walking command. If the muscle tension level within the muscle group exceeds the lower threshold of Z1 of the second controller, not only does the actuation of the "W" input occur in accordance with the first controller, but also the actuation of the "A" input occurs in accordance with the programming for the second controller. In the present example, this combination of keystrokes is associated with a leftward-forward walking command. As the muscle tension level continues to rise into Z2 of the second controller, the actuation of the "spacebar" input of the second controller is combined with the "W" input of the first controller, the combination of which results in a forward jump command. However, if the muscle tension level rises sufficiently to exceed the threshold of Z2 of the first controller, only the spacebar is actuated in accordance with the programming for the first and second controllers, resulting in only a vertical jump command. Finally, if the muscle tension level continues to rise into Z3 of the first controller, the actuation of the "S" input of the first controller is added to the "spacebar" input of the second controller, the combination of which results in a rearward jump command. In these substantially simultaneous modes of operation, the only limitation of the transfer rate is from the input device to the computer.

Figure 4:
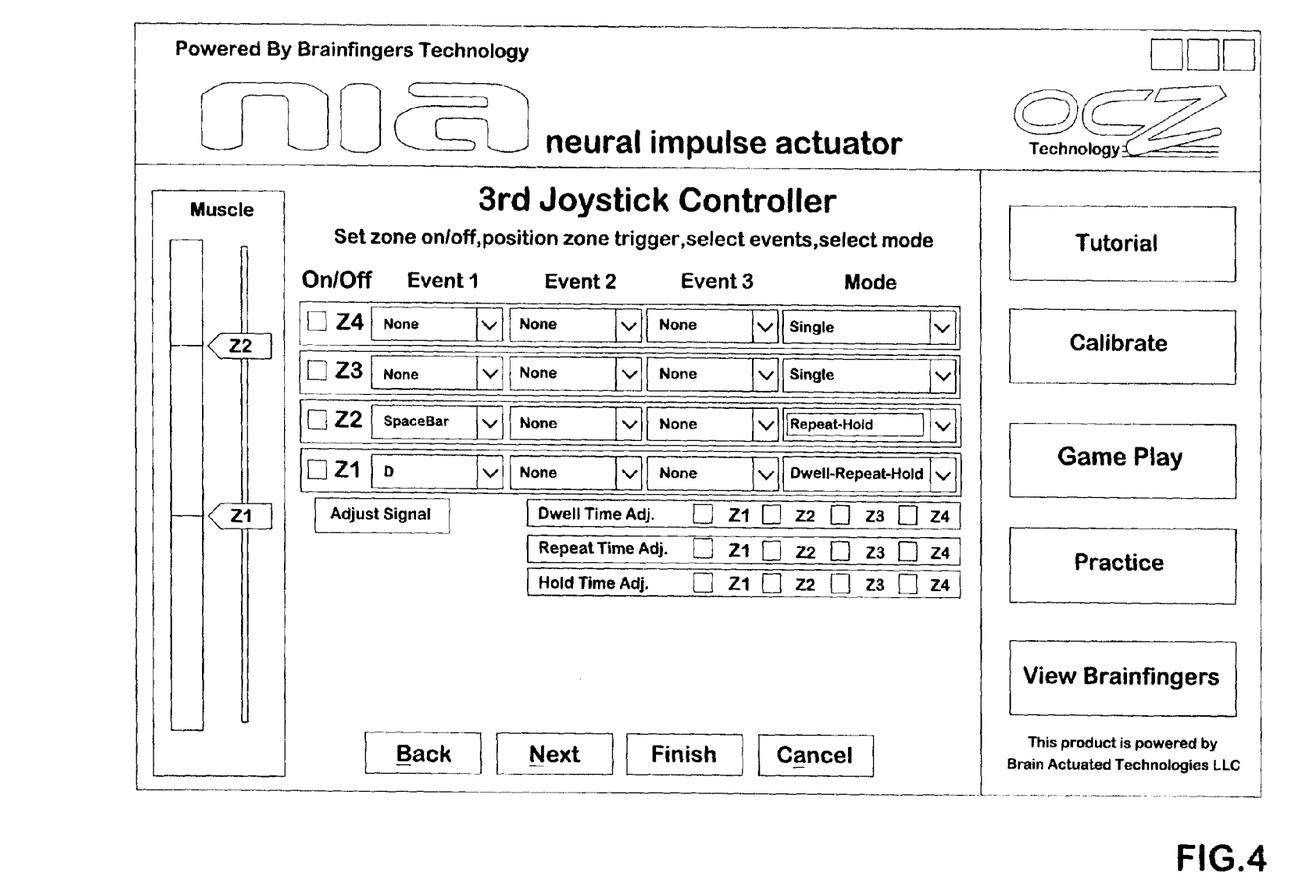

In the present example of FIGS. 2 through 4, the third parallel joystick controller has also been assigned to generate the same "spacebar" signal within its Z2 level for muscle tension. However, its Z1 level has been bound to a different keystroke: the "D" keyboard character. As a result, four combinations of three quasi-simultaneous key strokes are made available based on a single muscle tension input: a muscle tension level that simultaneously lies within Z1 of the first, second and controllers, a muscle tension level that simultaneously lies within Z1 of the first controller and Z2 of the second and third controllers, a muscle tension level that simultaneously lies within Z2 of the first controller and Z2 of the second and third controllers, and a muscle tension level that simultaneously lies within Z3 of the first controller and Z2 of the second and third controllers. By setting the level thresholds different for the different control channels and assigning different modalities, for example, setting "Delay," "Hold" and/or "Repeat" modes for each keystroke, a combination of keystrokes equivalent to a macro function can be emulated even in applications that do not support macros.

Figure 5:
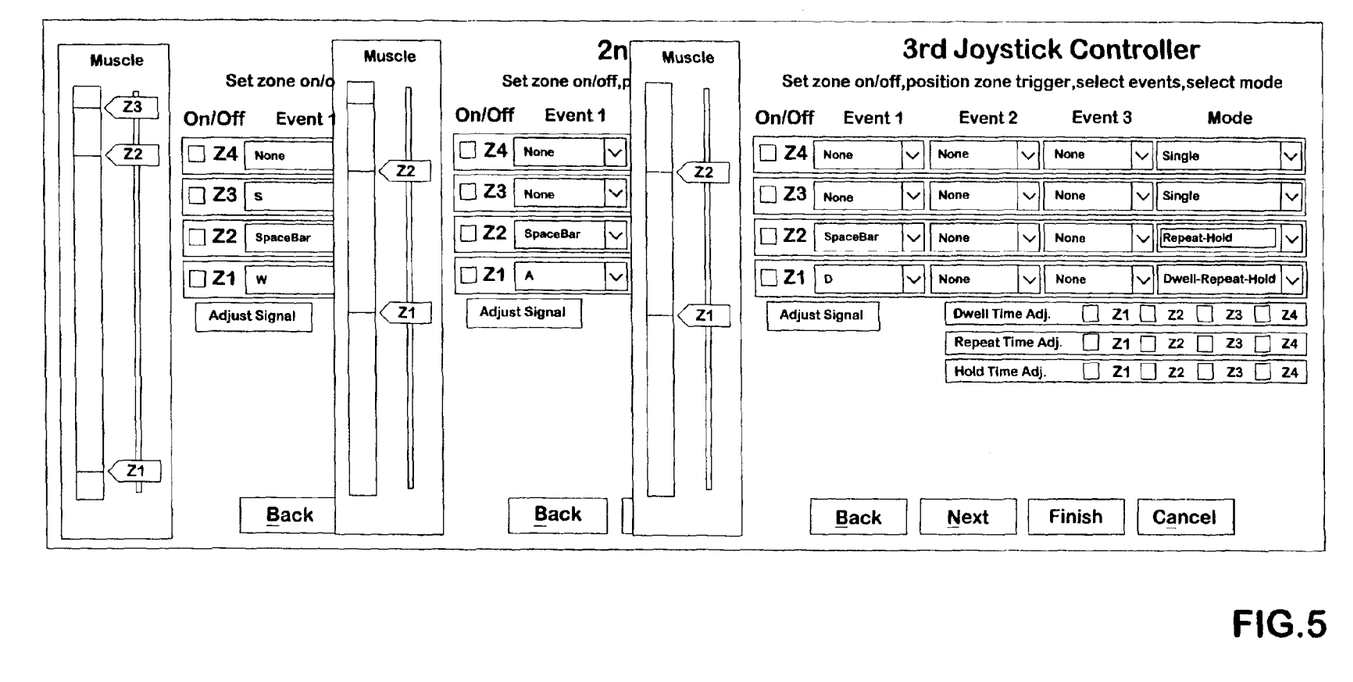
FIG. 5 is a screen shot of three tiled configuration panels generated by the software, and shows a summary of the overlap of the individual zones and identifies the various commands (actions) that will be input into the gaming application as a result of the simultaneous action of multiples of the keystrokes of the keyboard characters assigned in FIGS. 2 through 4.

The same command button can be used in multiple instances on the same or on parallel controllers. For example, the "spacebar" can be assigned to a zone of the first controller corresponding to a muscle tension level from 40% to 60% on the scale, and another zone corresponding to a muscle tension level from 80% to 100% on the first controller. In this manner, a desired action sequence can be easily created, for example, walk forward-jump forward-walk backward-jump backward, by overlapping the two spacebar zones of the first controller with a forward input command zone (e.g., from 20% to 60%) and a backward input command (e.g., 60% to 100%) zone of a different controller. Any other combination of keystrokes supported by the application is possible and can be implemented at the user's discretion. One such example is represented in FIG. 5 to include an actuation sequence of no action, run (or walk) forward (Z1 of the first controller only), run zigzag (alternating left and right) forward (Z1 of the first, second and third controllers), jump forward (Z1 of the first controller and Z2 of the second and third controllers), jump still (Z2 of the first, second and third controllers), and jump backward (Z3 of the first controller and Z2 of the second and third controllers).

Figure 6:
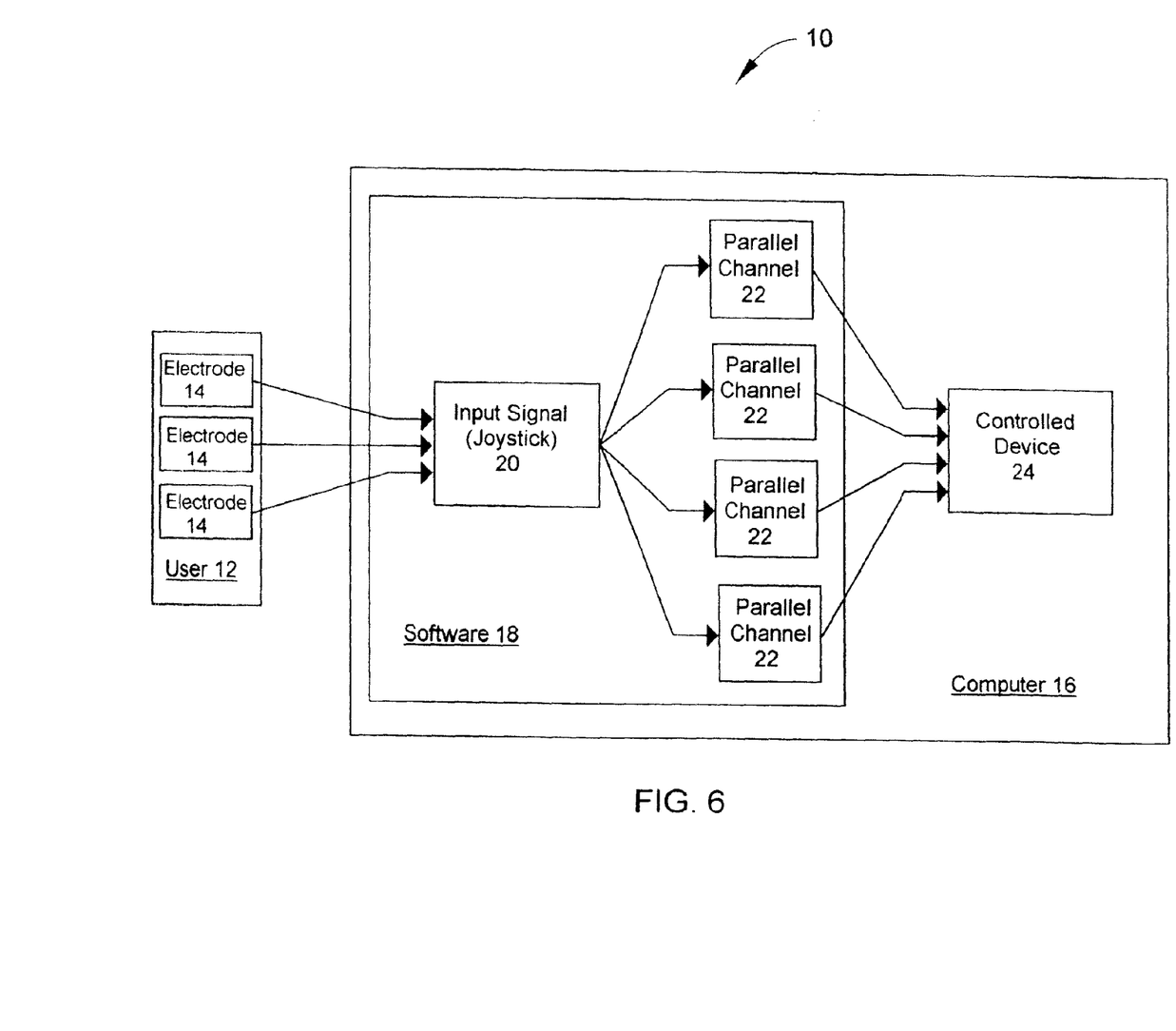
FIG. 6 is a block diagram representing a biosignal-computer-interface apparatus in accordance with an embodiment of the present invention.

In view of the foregoing, FIG. 6 a block diagram representing an embodiment of a biosignal-computer-interface apparatus 10 capable of using a substantially uniform biosignal input to generate an electrical signal corresponding to physiological parameters of a user 12, for example, biopotentials generated by the muscles, nerves and/or skin of the user 12. The biosignal input can be isolated from noise and other signals using standard methods, for example, as described in U.S. Pat. Nos. 5,474,082, 5,692,517 and 6,636763, the contents of which are incorporated herein by reference. The biosignal input can be sensed by one or more non-invasive electrodes 14 of a well-known type, though the use of other types of electrodes are also within the scope of the invention. The outputs of the electrodes 14 will typically produce analog signals that can be digitized and sent to a computer 16, which as used herein includes general-purpose computers (for example, personal computers (PCs)), special-purpose computers, peripheral computer hardware, specialized hardware, or any other computing/processing equipment that can be manufactured or modified to be programmed and configured for performing the multiple tasks through or with a computer or any other computer-related technology. The outputs of the electrodes 14 can be transmitted through a serial interface or any other suitable interface, including but not limited to USB, Bluetooth, and IEEE1394 Firewire interfaces. Software 18 (for example, gaming software) is represented as running on the computer 16 to transform the individual electrode output signals into a single input signal 20, for example, corresponding to the muscle joystick assigned in FIG. 1, that reflects signal strength. The software 18 can also be used to calibrate the signal 20 to reflect or adjust for properties of the individual user, such as the maximum muscle tension that the user can generate for the purpose of establishing the upper end of the 0 to 100 scale, as well as environmental parameters like relative humidity and temperature that can impact the electrical properties of the skin. The 0 to 100 scale range of the signal 20 can then be subdivided into individual signal levels, typically in a linear or logarithmic scale. In FIGS. 2 through 4, muscle tension is shown in the form of a sliding bar scale, though a dial or any other suitable visual representation could be used.

The software 18 is then used to multiply the signal 20 into any desired number of multiple parallel control channels 22 corresponding to the virtual joystick controllers of FIGS. 1 through 5. The control channels 22 can be defined by the software 18 and preferably use substantially the same scale based on the 0 to 100 scale range of the signal 20. As a result, the muscle tension level used as the input to the parallel channels 22 is preferably always the same. Each individual channel 22 can then divide the scale into multiple zones spanning from a no/low tension level to a high tension level, with each zone for each channel 22 being assigned to a keyboard character (or, in the case of a game application that can or requires use of a different controller device, some other type of control button, trigger, etc.) that when actuated produces a command output. Finally, the command outputs of the channels 22 can be used to control a game 24 running on the computer 16 or possibly another computer device in communication with the computer 16. Alternatively and as previously noted, the command outputs could be used to control other types of devices and equipment, including but not limited to communication devices, vehicles, and weapon systems.

The ability to add "Dwell," "Repeat" and "Hold" modalities to the keys provides an extension to the versatility of the invention. For example, FIG. 2 indicates the first controller as being configured to entail a "Hold" parameter assigned to the "W" key, a "Repeat-Hold" parameter assigned to the "spacebar" key, and a "Dwell-Repeat-Hold" parameter assigned to the "S" key. The result would be that the game's graphical representation (avatar) constantly walks forward until the signal reaches the threshold for Z2, followed by initiating the "spacebar" key for jumping at a repeat frequency with a specified hold down duration, both of which are preferably defined by the user. Once the signal reaches the threshold for Z3, the "S" key for walking backward is initiated. However, because of the dwell function, the actual transmission of the command is delayed until the dwell interval (preferably defined by the user) is satisfied. After the initial dwell delay, the signal is repeated at the repeat frequency and hold down duration defined by the user. As a result, the player can define a delayed, slow retreat, in combination with any other controls defined on the second controller using a single input signal. Any other combination of modalities in combination with different keystrokes across a plurality of controllers is possible as long as the application supports it.

A variation of the scheme outlined above could be to assign the same key to multiple zones within one controller, but setting different repeat intervals and hold durations for the individual zones. Using a gradual increase in keystroke frequency, a controller using the "W" key can easily be configured to work like an accelerator in a racing game where power-slides and spin-outs can be triggered by assigning "S" or break commands on a parallel control channel. Another example would be gear-shift commands in combination with acceleration and breaking on a parallel control channel.

In view of the above, the present invention provides a number of advantages, including: ease of use of a hands-free interface between biosignals and a computer; arbitrary triggering of response based on voluntary muscle tension, precise timing of the trigger events, multi-functionality of the same trigger zone through overlapping command signal assignment in parallel control channels, and flexible configuration of the command structure through arbitrary assignment of command signals and command modes.

While the invention has been described in terms of particular embodiments, it is apparent that other forms could be adopted by one skilled in the art. Therefore, the scope of the invention is to be limited only by the following claims.

The invention claimed is:

1. A method of using a biosignal-computer-interface apparatus comprising:
   converting at least a first biopotential into at least a first input signal with a computer-interface means;
   multiplying the first input signal into multiple parallel control channels;
   assigning multiple computer commands to multiple individual zones of the multiple parallel control channels;
   generating at least one of the computer commands if the input signal exceeds a threshold of at least one of the individual zones of the parallel control channels; and
   simultaneously generating the computer commands assigned to two or more of the individual zones of two or more of the parallel control channels if the input signal is within the two or more individual zones;
   wherein the first biopotential is generated by muscle tension of the individual, the input signal corresponds to sensed muscle tensions of the individual, the different levels of the input signal are within a range of the sensed muscle tensions of the individual encompassed by the scale, and the individual zones of each parallel control channel are discrete muscle tension level ranges within the range of the sensed muscle tensions of the scale.

2. The method according to claim 1, further comprising generating the first biopotential as one of a plurality of biosignals based on at least one physiological parameter of an individual.

3. The method according to claim 2, wherein the biosignals are generated with non-invasive electrodes placed on the skin of the individual.

4. The method according to claim 1, further comprising:
   establishing a scale encompassing different levels of the input signal; and
   dividing the scale into the individual zones of each of the parallel control channels.

5. The method according to claim 1, further comprising assigning different modalities to each of the computer commands.

6. The method according to claim 5, wherein the different modalities include at least one modality chosen from the group consisting of single, dwell, repeat, and hold functions.

7. The method according to claim 1, wherein the computer commands assigned to the individual zones of the parallel control channels correspond to keystrokes of a computer keyboard.

8. The method according to claim 7, further comprising assigning different modalities to at least two of the computer commands.

9. The method according to claim 8, wherein the different modalities include at least one keystroke modality chosen from the group consisting of single, dwell, repeat, and hold keystrokes.

10. The method according to claim 1, wherein at least one individual zone of the individual zones of a first of the parallel control channels is different than at least one individual zone of the individual zones of a second of the parallel control channels, and the generated computer commands comprise at least one computer command that is a combination of the computer commands assigned to the at least one individual zone of the first parallel control channel and the at least one individual zone of the second parallel control channel.

11. The method according to claim 1, further comprising using the computer commands to control a device chosen from the group consisting of computer, communication device, vehicles, and weapon systems.

12. The method according to claim 1, further comprising using the computer commands to control a computer game.

* * * * *